United States Patent [19]

Chen et al.

[11] Patent Number: 4,476,334
[45] Date of Patent: Oct. 9, 1984

[54] METHANOL PRODUCTION METHOD AND SYSTEM

[75] Inventors: Michael J. Chen, Darien; Jerome W. Rathke, Bolingbrook, both of Ill.

[73] Assignee: The United States Department of Energy, Washington, D.C.

[21] Appl. No.: 498,437

[22] Filed: May 26, 1983

[51] Int. Cl.³ .......................... C07C 29/00; B01J 31/02
[52] U.S. Cl. ....................................... 568/902; 502/161
[58] Field of Search ......................... 568/902; 502/161

[56] References Cited

U.S. PATENT DOCUMENTS

| | | | |
|---|---|---|---|
| 3,248,432 | 4/1966 | Riley et al. | 568/902 |
| 4,152,248 | 5/1979 | Feder et al. | 208/144 |
| 4,301,312 | 11/1981 | Feder et al. | 568/902 |
| 4,320,230 | 3/1982 | Doyle | 568/902 |
| 4,386,009 | 5/1983 | Feder et al. | 568/902 |
| 4,415,749 | 11/1983 | Hargis et al. | 568/902 |

OTHER PUBLICATIONS

Koermer et al., "Ind. Eng. Chem. Prod. Res. Dev.", vol. 17, No. 3, 1978, pp. 231–236.

*Primary Examiner*—J. E. Evans
*Attorney, Agent, or Firm*—Hugh W. Glenn; Robert J. Fisher; Michael F. Esposito

[57] ABSTRACT

Ethanol is selectively produced from the reaction of methanol with carbon monoxide and hydrogen in the presence of a transition metal carbonyl catalyst. Methanol serves as a solvent and may be accompanied by a less volatile co-solvent. The solution includes the transition metal carbonyl catalysts and a basic metal salt such as an alkali metal or alkaline earth metal formate, carbonate or bicarbonate. A gas containing a high carbon monoxide to hydrogen ratio, as is present in a typical gasifier product, is contacted with the solution for the preferential production of ethanol with minimal water as a byproduct. Fractionation of the reaction solution provides substantially pure ethanol product and allows return of the catalysts for reuse.

13 Claims, 1 Drawing Figure

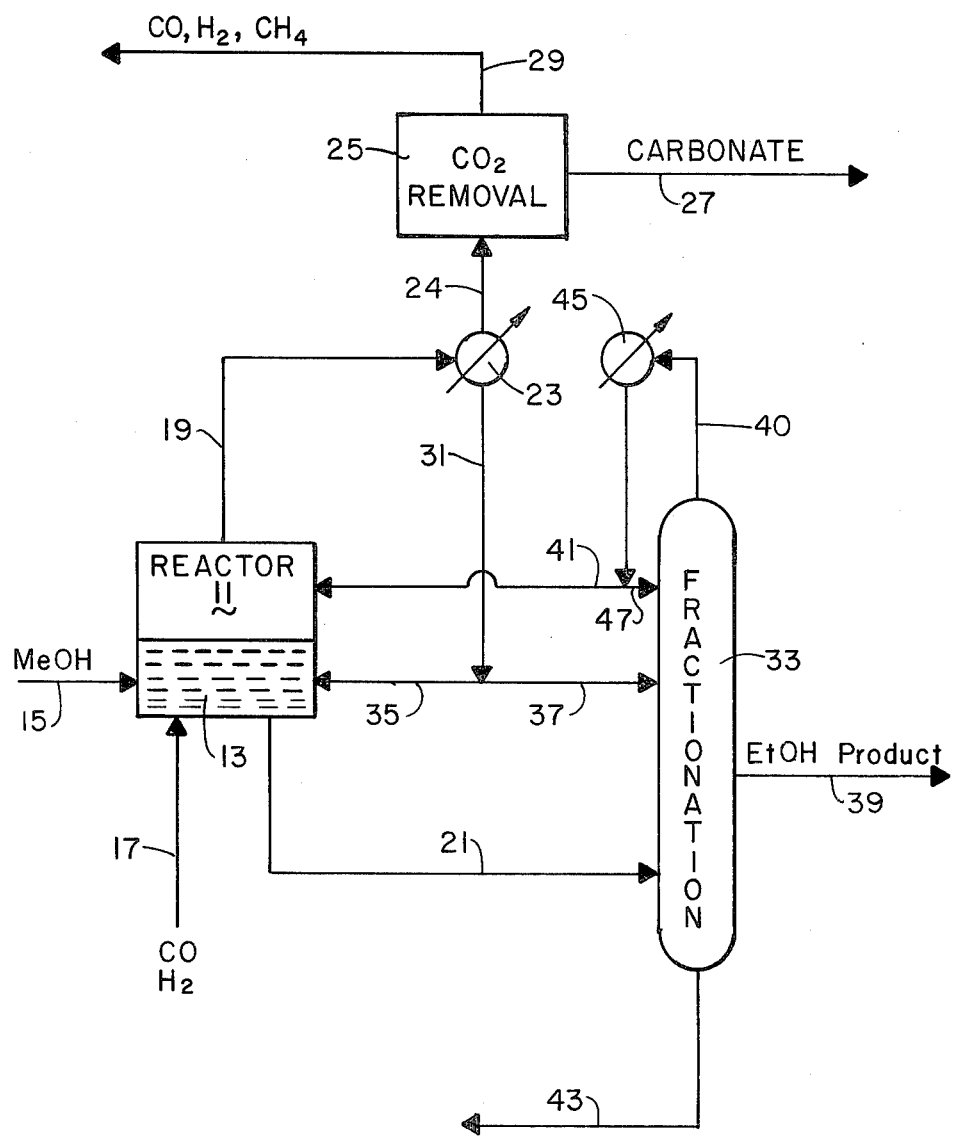

METHANOL PRODUCTION METHOD AND SYSTEM

CONTRACTUAL ORIGIN OF THE INVENTION

The United Stated Government has rights in this invention pursuant to Contract No. W-31-109-ENG-38 between the U.S. Department of Energy and Argonne National Laboratory.

BACKGROUND OF THE INVENTION

The present invention relates to a method and to a system for the production of ethanol. It is particularly applicable to the conversion of methanol to ethanol but also relates to the production of ethanol from gases including carbon monoxide and hydrogen. It is of note that methanol itself is derived from these gases. Such gases are produced in the gasification of coal or other carbonaceous material. Where carbon monoxide and hydrogen along with various gasifier products are provided as raw materials, methanol or a methanol derivative such as methyl formate is contemplated as a reactant or as an intermediate within the process and system of the present invention. Therefore, the present process and system will be described in most instances in terms of the conversion of methanol to ethanol. The catalytic system used is a homogenous system with transition metal carbonyl catalysts in organic liquid solution. In previous systems, cobalt carbonyls in organic solvents have been used as catalysts for the reaction of methanol with carbon monoxide and hydrogen gas. In such reactions both ethanol and water were produced along with a large variety of byproducts including various ethers, esters, acetals and higher alcohols.

In previous work at the Argonne National Laboratory, a system and method were developed for the production of ethanol with minimal production of water as a byproduct. The catalytic system involved the use of various transition metal carbonyls other than cobalt within organic solvent and in combination with a tertiary amine. Carbonyls of iron, manganese, rhodium, osmium and ruthenium were suggested as catalysts. Although these methods provide good yield and high selectivity for ethanol the various tertiary amines have a tendency to degrade at high temperature. The presence of the amine complicates the final separation of ethanol from the reaction mixture to increase production costs. In addition the various amines employed are expensive.

The following patents and other publications are illustrative of the general field of the present development:

U.S. Pat. No. 4,301,312 to Feder and Chen, "Method and System for Ethanol Production", 1981. This patent discloses the use of a transition metal carbonyl catalyst and a tertiary amine for the conversion of methanol to ethanol.

U.S. Pat. No. 4,152,248, "Hydrogenation of Coal Liquid Utilizing a Metal Carbonyl Catalyst". This patent discloses a method in which coal liquid is hydrogenated in the presence of a transition metal carbonyl catalyst and a dissociating solvent.

U.S. patent application Ser. No. 305,295 allowed Dec. 3, 1982, "Method and System for Ethanol Production". This patent application is a continuation-in-part of U.S. Pat. No. 4,301,312. It discloses particular combinations of transition metal carbonyl catalysts and tertiary amines for the production of ethanol.

Industrial Engineering Chemistry Production, Research, and Development, Vol. 17 No. 3, 1978, pp. 231–236, disclose conversion of methanol to ethanol in organic solution with the cobalt carbonyl catalysts. Water and various other organic compounds are also produced.

In describing the present invention, the following abbreviations or symbols will be used:

Me—Methyl group, $CH_3$

Et—Ethyl group, $C_2H_5$ pka—The negative logarithm of the acid dissociation constant for the acid, HB in water where $B^-$ is the conjugate base, i.e.

$$-pKa = \text{Log}\left(\frac{[H_3O^+][B^-]}{[HB]}\right)$$

Since the catalytic system of this application is in organic solution rather than water, pKa is used as an estimate of relative acidity or basicity.

pH—For purposes of this application, pH refers to actual measurements in organic solutions with commercially available pH meters rather than to the negative logarithm of the hydronium ion concentration which may not be present in the solution.

SUMMARY OF THE INVENTION

Therefore in view of the above it is an object of present invention to provide a method for the selective production of ethanol with minimal production of water.

It is a further object to provide an ethanol production method in which methanol is combined with carbon monoxide and hydrogen in homogenous organic solution with catalysts.

It is a further object to provide an ethanol production method in organic solution permitting a simplified fractionation step in the recovery of ethanol.

It is also an object to provide an ethanol production method that minimizes or eliminates expensive tertiary amines from the homogenous catalytic solution.

It is yet another object to provide a catalytic system for the production of ethanol from methanol, carbon monoxide and hydrogen in which costly tertiary amines are not present and in which subsequent fractionation separations are facilitated.

In accordance with the present invention, a method of selectively producing ethanol from methanol, carbon monoxide and hydrogen with minimal production of water is presented. The method is performed in organic solution including methanol solvent and a transition metal carbonyl catalyst along with a metal formate, metal carbonate or a metal bicarbonate of the alkali or alkaline earth metals. The homogenous catalytic solution is contacted with carbon monoxide and hydrogen to produce ethanol and carbon dioxide.

In more specific aspects of the invention sufficient metal formate, metal carbonate or metal bicarbonate of the alkali or alkaline earth metals or mixtures thereof is provided to increase the basicity of the solution and thereby promote the formation of methyl formate from methanol and carbon monoxide. In such a solution the basicity is sufficient to stabilize a nucleophilic transition metal carbonyl species capable of undergoing methylation.

In further aspects of the invention the bascity of the solution is adjusted by the addition of soluble alkali metal salts of formate, carbonate, bicarbonate or mixtures thereof.

In other more specific aspects, transition metal carbonyl catalysts selected from the manganese carbonyls, iron carbonyls, ruthenium carbonyls, rhodium carbonyls, osmium carbonyls and mixtures of these catalysts are included in solution. Preferably a manganese carbonyl is included.

In other aspects, the homogenous catalytic solution includes not only methanol as solvent but a co-solvent that is less volatile that either methanol or ethanol. Also, the reaction of the catalytic solution with carbon monoxide and hydrogen gas can be carried out at a temperature of 200°–300° C., preferably about 220° C. and a pressure of 100–400 atmospheres, preferably about 200 atmospheres.

Applicant's invention also is contemplated as a homogenous catalytic system in organic solvent including methanol having in solution a transition metal carbonyl catalyst and a basic metal salt selected from alkali metal carbonates, alkaline earth metal carbonates, alkali metal bicarbonates, alkaline earth metal bicarbonates, alkali metal formates, alkaline earth metal formates and mixtures thereof.

In more specific aspects of this system alkali metal formate is included at a concentration of about 0.1–1 mole per liter and the system further includes in solution carbon monoxide, hydrogen, a nucleophilic species of transition metal carbonyl capable of being methylated.

Additional objects, advantages and novel features of the invention will be set forth in part in the description which follows and in part will become apparent to those skilled in the art upon examination of the following or may be learned by practice of the invention.

BRIEF DESCRIPTION OF THE DRAWINGS

The FIGURE is a diagrammatic flow diagram illustrating a process for converting methanol to ethanol.

DETAILED DESCRIPTION OF THE PREFERRED EMBODIMENT

In carrying out the method of the present invention, the constituents of the reaction for the selective production of ethanol are combined within a homogenous organic solution. Methanol, one of the principle materials for reaction, may be employed as organic solvent as will be discussed below. Less volatile co-solvents also may be advantageously employed. The other principle reactants, carbon monoxide and hydrogen can readily be dissolved into solution by contact with a gas containing these reactants. The catalysts for this reaction system is a transition metal carbonyl or mixtures of a plurality of transition metal carbonyls. Although the catalysts do not enter into the overall reaction, it will be suggested below that methylated intermediates of the catalysts promote the reaction.

Applicant's novel method and system are advantageous selected over previously known processes in that expensive and decomposable amines are no longer required in the catalytic system. Applicants substitute a basic alkali metal salt or alkaline earth metal salt, instead of the previously used tertiary amines, to promote the catalytic and selective production of ethanol. The salt is selected from the alkali metal or alkaline earth metal formates, carbonates or bicarbonates.

The homogeneous catalytic system and the reaction not only does not produce water but is advantageously operated and provided with constituents having minimal water content. Dry solvents and reaction mixtures are preferably employed but constituents and mixtures with up to about 4 weight percent water are contemplated in the production of ethanol.

Although the catalytic system in which the reaction occurs is contemplated as a homogenous system, a plurality of liquid phases or solids including co-solvents, transition metal carbonyls and the basic metal salt beyond their solubility in the principle solvent also may be provided for maintaining ample concentration of the various constituents in the principal reaction solution.

An important aspect of the catalytic system and process is the appropriate selection of the transition metal carbonyl. The selected transition metal carbonyl must operate in the organic solution to provide the necessary catalytic species and intermediates for selectively producing ethanol substantially to the exclusion of water. A strong nucleophilic species of the transition metal carbonyl is in the solution to become methylated by interaction with such as methyl formate and subsequently react with carbon monoxide and hydrogen to provide ethanol. Although a number of transition metal carbonyls are contemplated for use, the carbonyls of manganese are preferred.

The following reactions involving the reactants and species of manganese carbonyl catalyst are offered as one explanation of the chemistry involved in the method and system of the present invention. However, this series of reactions is only one theory of how applicants' method operates for the production of ethanol. Consequently, the inventors do not wish to be limited to these equilibria and reactions as the complete or exclusive paths by which the present catalytic system and method operate.

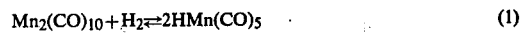

$$Mn_2(CO)_{10} + H_2 \rightleftharpoons 2HMn(CO)_5 \qquad (1)$$

$$HMn(CO)_5 + HCO_2^- \rightarrow H_2 + CO_2 + Mn(CO)_5^- \qquad (2)$$

$$MeOH + CO \xrightarrow{Base} HCO_2Me \qquad (3)$$

$$Mn(CO)_5^- + HCO_2Me \rightarrow MeMn(CO)_5 + HCO_2^- \qquad (4)$$

$$MeMn(CO)_5 + CO + 2H_2 \rightarrow MeCH_2OH + HMn(CO)_5 \qquad (5)$$

The net reaction for (2)–(5) is:

$$MeOH + 2CO + H_2 \rightarrow MeCH_2OH + CO_2 \qquad (6)$$

Methyl formate is the methylating agent in this catalyst system and donates the methyl cation to the pentacarbonyl manganese anion as is shown in reaction (4).

It is expected that any of the alkali metal formates including potassium formate, sodium formate and lithium formate are sufficiently soluble in methanol and the co-solvents discussed below to promote the production of ethanol. In addition to alkali metal formates, alkaline earth formates such as calcium formate or magnesium formate also may be suitable. However, due to the limited solubility of alkaline earth metal formates in some solution the alkali metal formates are preferred for use.

It has been found that formate ion concentrations of 0.1–1 mole per liter in the organic solution are suitable for use. It is expected that concentrations much below 0.1 per liter would not provide sufficient basicity and concentrations higher than 1 mole per liter would be redundant and wasteful, possibly increasing the risk of solid precipitation.

The reactions presented above illustrate the presence of formate ion in solution for the production of the pentacarbonyl anion (reaction 2). However, in systems beginning only with carbonate or bicarbonate anions as is also contemplated, the pentacarbonyl anion may result from their analogous reaction with the protonated pentacarbonyl.

Although the reactions have been presented in terms of manganese carbonyl catalysts, it is expected that various other transition metal or noble metal carbonyls may also be selected to provide sufficient catalytic activity in the method and system of the present invention. The assignees patent cited above disclosed carbonyls of ruthenium, iron, osmium, rhodium, and combinations of these transition metal carbonyls for catalytic activity in systems employing a tertiary amine in organic solution. It is reasonable to expect that certain of these carbonyls also will catalytically promote ethanol production in the present method and system.

Certain carbonyls such as $Fe(CO)_5$ require a somewhat higher basicity than that of the formate system. The catalyst solution with dissolved formate salt has been found to have a measured pH of about 7 or slightly higher. The pentacarbonyl manganese anion is stable in such a solution as its conjugate protonated species, $HMn(CO)_5$ has a pKa of about 7. However, it has been found that in the formate system the nucleophilic species of $HFe(CO)_4^-$ is converted to the inactive $Fe(CO)_5$ species. It is thus expected that systems using the iron carbonyl catalysts or other catalysts which require a somewhat more basic solution than that provided with formate ion, must be modified to increase the basicity. To do this the carbon dioxide product gas can be rapidly and thoroughly removed or a buffer solution of alkali metal bicarbonate or carbonate can be added into the organic solution to increase the pH.

The co-solvent selected for use with methanol in the catalytic system and method of the present development is one that generally is unreactive with the constituents of the solution. Methanol can be selected as the solvent used with a co-solvent. Co-solvents with higher boiling points than methanol or ethanol are preferred to provide a stable catalytic liquid solution as reaction vapor is withdrawn. Suitable co-solvents contemplated are dimethylether of diethylene glycol (diglyme), ethoxyethanol, tetraglyme, butanol, other higher alcohols or glycols, decalin, N-methylpyrrolidinone-2, tetrahydrothiophene-1,1-dioxide and mixtures of these various co-solvents. Other co-solvents contemplated are N,N-dimethyl-formamide, N,N-dimethylacetamide and their higher homologs.

The catalytic method and system of the present invention can be carried out at a somewhat higher temperature than that of previous methods which employ tertiary amines in the catalytic reaction solution. This advantage is brought about as the formates, carbonates or bicarbonates substituted for the amines are less likely to decompose at these higher temperatures. Therefore, temperatures of 200°–300° C. at pressures of 100–300 atmospheres are contemplates for the present invention.

Preferably, temperatures of about 220° C. and pressures of about 200 atmospheres are selected.

One manner of performing the method of the present invention is now described by reference to the FIGURE. A reactor 11 contains the homogeneous liquid catalytic system 13 as described in detail above. Anhydrous methanol or methanol with no more than 4% water enters at line 15. A gas mixture of carbon monoxide and hydrogen enters the reactor in line 17. Such gas mixutres can be conveniently provided from the gas product of a coal or other carbonaceous material gasification process in which the carbon monoxide is typically present in about 2 to 3 times that of the hydrogen partial pressure. This provides a slight excess in the 2:1 stoichiometric carbon monoxide to hydrogen requirement of the overall reaction of the present invention.

The methanol provided in line 15 may be from a number of commercially known sources and processes. For instance, methanol can be produced by disstillation of the fermentation product of wood or other biomass. It is also available in the catalytic hydrogenation of carbon monoxide, for instance, by passing the hydrogen enriched products of a coal gasifier over a suitable metal oxide e.g. copper-zinc chromite catalysts. Should methanol be prepared from this gasifier product, excess carbon monoxide and hydrogen that remain unreacted may be passed directly upon compression into reactor 11 of the present process. Since methanol is converted to methyl formate by its reaction with carbon monoxide in the reaction series resulting in ethanol, methyl formate may be provided with or in place of the methanol. For instance, the initial reactor charge may be provided with methyl formate.

The ethanol produced in the reactor can be removed for further separation by withdrawing vapor through line 19 or by withdrawing liquid through line 21. It is preferred that this withdrawal be made from the vapor phase to eliminate or reduce the need to separate and recycle catalyst and high boiling solvent to the reactor. The vapor flow passes through a condenser 23 with the noncondensable gases including the carbon dioxide produced passed through line 24 to an acid gas separation unit 25 such as a scrubber or an adsorpsion unit where the carbon dioxide can be removed at 27. The remaining gases such as unreacted carbon monoxide and hydrogen as well as by-products, for instance methane, can be withdrawn in line 29 for other use or recycle into the reactor. If the gas stream includes substantial amounts of methane, it can be steam reformed to hydrogen and carbon monoxide and dried prior to recycle to reactor 11. Alternatively, the gas flow may be suitable as a fuel for other process requirements.

The condensate 31 from condensor 23 may be recycled into the reactor through line 35 or fed into a fractionation column 33 through line 37 depending on its composition. For instance, if the condensate includes large amounts of ethanol it can be fed to the fractionation column 33. However, if it is primarily methanol, it can be returned to reactor 11 through 35. It may be desirable to split the flow of condensate with portions to both the reactor and to the fractionation column.

The liquid withdrawn through line 21 can be fed into fractionation column 33 at a lower level than the feed point of the condensed vapors at 37. The withdrawal through line 21 may or may not be necessary depending on whether a sufficient flow of ethanol can be withdrawn with the vapor stream through line 19.

Fractionation column 33 is used to separate the ethanol product at 39 from methanol and from the less volatile solvents and catalysts. The methanol is withdrawn from the top of the column at 40 and the less volatile materials are withdrawn from the bottom at line 43. The high boiling materials at 43 can include the transition metal carbonyl, the basic metal salt and high boiling solvents. This stream at 43 will ordinarily be recycled to the reactor 11 with any needed make up or upgrading of solvent or catalyst. The reflux condensor 45 is illustrated at the top of fractionated column 33 for providing a liquid reflux 47 and the recycled stream 41 for returning methanol to reactor 11.

Although the present process is described above in terms of a continuous reactor and fractionation unit to separate the ethanol product, it will be clear that various other unit operations and process steps well known in the art can also be employed. For example, the reaction may be performed in batch reactors with liquid products subsequently removed for separation in batches or with a plurality of batch reactors alternately feeding the continuously operating separation column. A separate reactor can be provided to convert methanol at least partly to methyl formate. It also may be advantageous to employ a series of reactors to incrementally increase the ethanol concentration within the liquid and/or gas phase prior to the final fractionation separation. As discussed above, the feed to the fractionation column may be from either or both the gas or liquid phases from the reactor and various streams within and from the process may either be recycled into the reactor or employed for beneficial purposes as will be apparent to one skilled in the art.

The following examples are presented merely to illustrate but not to limit the scope of the present invention.

EXAMPLE I (M-124)

An organic solution including about 0.075M $Mn_2(CO)_{10}$ and about 0.2M $HCO_2K$ in methanol was used as the catalytic solution for contact at 200° C. and 300 atmospheres pressure with the gas mixture of 3 mole parts carbon monoxide to 1 mole part hydrogen. After about 7 hours operation the solution contained about 2.5M ethanol. Table I below gives further results of this run.

TABLE I

| t,h | $[Mn(CO)_5]^-$ M | $[HCO_2Me]$ M | $[EtOH]$ M | $[HCO_2Et]$ M |
|---|---|---|---|---|
| 0.05 | 0.124 | 0.80 | 0.16 | 0.01 |
| 0.25 | 0.124 | 0.85 | 0.30 | 0.02 |
| 1.33 | 0.094 | 0.85 | 0.84 | 0.04 |
| 2.33 | 0.078 | 0.78 | 1.36 | 0.07 |
| 4.33 | 0.060 | 0.82 | 1.99 | 0.10 |
| 7.00 | 0.044 | 0.90 | 2.53 | 0.13 |

EXAMPLE II (M-123)

The method and system of Example I was carried out with the addition of about 0.1M $Fe(CO)_5$ to the organic solution. After about 9 hours, approximately 2.7 moles per liter ethanol was produced. The rate of ethanol production was not significantly distinguishable from that obtained without the iron carbonyl additive.

EXAMPLE III (M-125)

The method of Example I was performed with 0.3 moles per liter potassium iodide. Ethanol production was nearly identical to that of Example I.

EXAMPLE IV (M-126)

A methanol solution containing 0.1M $Fe(CO)_5$ and 0.5M $HCO_2K$ was operated as in the previous example, except temperatures of 200° C., 230° C. and 260° C. were used. It was found that the iron carbonyl catalysts decompose to iron metal at 260° C. After 4 hours exposure to hydrogen and carbon monoxide gas, the ethanol concentration was only at 0.01 molar showing the ineffectiveness of this iron carbonyl species at an unadjusted pH to produce ethanol. However, the gas above the solution contained more than 11 mole percent methane and 23 mole percent carbon dioxide. It is expected that by increasing the system pH, for instance by appropriate purging of $CO_2$ gas, that increased selectivity of ethanol over methane can be obtained.

In each of the above examples in which significant ethanol was produced, it was found that only minimal quantities of water was present and that the gases produced by the reaction contained substantial quantities of carbon dioxide as one of the reaction products. Some methane also was produced as a by-product of the reaction.

It will therefore be seen that ethanol can be produced from methanol by reaction with carbon monoxide and hydrogen without the need for expensive and difficult to handle tertiary amines. The problems arising from the decomposition of tertiary amines at high temperatures can therefore be eliminated in a process for the production of ethanol with limited or no water production.

It will therefore be clear that ethanol can be produced by the reaction of methanol or methyl formate with gases including carbon monoxide and hydrogen at partial pressures typical of those present in a gasifier product. The present process through use of the novel combination of alkali metal formates, carbonates or bicarbonates with transition carbonyl catalysts permits good selectivity of ethanol over other aliphatic compounds such as ethers, acetates, aldehydes and higher alcohols.

It will be clear that although the present method and system are described in terms of specific embodiments, that various changes in the materials, process steps and techniques can be made by those skilled in the art within the scope of the appended claims.

The embodiments of this invention in which an exclusive property or privilege is claimed are defined as follows:

1. In a method of selectively producing ethanol from methanol, carbon monoxide and hydrogen in the presence of a transition metal carbonyl catalyst in accordance with the reaction $MeOH + 2CO + H_2 \rightarrow EtOH + CO_2$ substantially without the production of water, the improvement comprising:

including in organic solution having methanol solvent, a base selected from the group of metal salts consisting of the alkali metal and alkaline earth metal formates, bicarbonates and carbonates; in combination with a manganese carbonyl catalyst in said solution; and contacting said solution with carbon monoxide and hydrogen to effect production of ethanol and carbon dioxide.

2. The method of claim 1 wherein said solution contains a sufficient concentration of said base to promote the formation of methyl formate from methanol and carbon monoxide.

3. The method of claim 2 wherein the basicity of said solution is sufficient to stabilize a nucleophilic transition metal carbonyl species capable of being methylated in said solution.

4. The method of claim 1 wherein said solution includes a co-solvent blended with methanol, said co-solvent being characterized by a lower vapor pressure than methanol or ethanol.

5. The method of claim 4 wherein said co-solvent is selected from the group of high boiling organic liquids consisting of dimethyl ether of diethelene glycol (diglme), ethoxyethanol, tetraglyme, butanol, higher homologs of ethoxyethanol and butanol, higher homologs of diglyme and tetraglynme, decalin and N-methylpyrrolidinone-2, tetrahydrothiophene-1, 1-dioxide-N,N-dimethylformamide, N,N-di-methyl-acetamide, higher homologs of said formamide and said acetamide, and mixtures of said high boiling organic liquids.

6. The method of claim 4 wherein said solution while in contact with carbon monoxide and hydrogen is at a temperature of 200°–300° C. and said hydrogen and carbon monoxide is a gas at a pressure of 100–400 atmospheres.

7. The method of claim 6 wherein said solution temperature is about 220° C.

8. The method of claim 6 wherein said gas pressure is about 200 atmospheres.

9. The method of claim 6 wherein said carbon monoxide and hydrogen are present in said gas at a molar ratio of about two parts carbon monoxide to one part hydrogen.

10. A method of selectively producing ethanol from methanol, carbon monoxide and hydrogen in the presence of a manganese carbonyl catalyst substantially without the production of water comprising, forming an organic solution including methanol with the manganese carbonyl species, $Mn_2(CO)_{10}$, $HMn(CO)_5$ and $Mn(CO)_5^-$ in combination with alkali metal formate in solution; and contacting said solution with carbon monoxide and hydrogen gas to effect production of ethanol and carbon dioxide.

11. In a homogenous catalytic system in organic solvent including methanol and a transition metal carbonyl catalyst in solution for the conversion of methanol to ethanol in accordance with the reaction:

$$MeOH + 2CO + H_2 \rightarrow EtOH + CO_2$$

the improvement comprising:

a manganese carbonyl catalyst in said solution; and a base selected from the group of metal salts consisting of alkali metal carbonates, bicarbonates and formates and alkaline earth metal carbonates, bicarbonates and formates in said solution.

12. The homogenous system of claim 11 wherein the base is alkali metal formate at a concentration of 0.1–1 mole per liter.

13. The homogenous system of claim 11 wherein said solution further includes dissolved carbon monoxide, hydrogen and a nucleophilic species of said manganese carbonyl catalyst capable of being methylated.

* * * * *